United States Patent [19]

Koci et al.

[11] 4,319,881

[45] Mar. 16, 1982

[54] PROCESS FOR PRINTING OR PAD DYEING OF TEXTILE MATERIAL MADE FROM CELLULOSE FIBRES, OR FROM MIXTURES THEREOF WITH SYNTHETIC FIBRES

[75] Inventors: Zdenek Koci, Binningen; Andres Schaub, Biel-Benken, both of Switzerland

[73] Assignee: Ciba-Geigy Corporation, Ardsley, N.Y.

[21] Appl. No.: 202,082

[22] Filed: Oct. 30, 1980

[30] Foreign Application Priority Data

Nov. 5, 1979 [CH] Switzerland ............... 9908/79

[51] Int. Cl.$^3$ .............................................. D06P 3/82
[52] U.S. Cl. .......................................... 8/532; 8/552; 8/564; 8/611; 8/918
[58] Field of Search ............... 8/532, 564, 611, 918, 8/552

[56] References Cited

U.S. PATENT DOCUMENTS

| | | | |
|---|---|---|---|
| 3,706,525 | 12/1972 | Blackwell et al. | 8/532 |
| 3,963,430 | 6/1976 | Nonn et al. | 8/564 |
| 3,968,104 | 7/1976 | Wagner | 546/243 |
| 4,038,198 | 7/1977 | Wagner et al. | 521/152 |
| 4,083,689 | 4/1978 | Wolf et al. | 8/564 |
| 4,120,648 | 10/1978 | Agarwal et al. | 8/564 |
| 4,132,523 | 1/1979 | Ong | 8/444 |
| 4,268,266 | 5/1981 | Hendricks et al. | 8/564 |

FOREIGN PATENT DOCUMENTS

| | | |
|---|---|---|
| 2643804 | 4/1978 | Fed. Rep. of Germany . |
| 2700150 | 7/1978 | Fed. Rep. of Germany . |
| 2751830 | 8/1978 | Fed. Rep. of Germany . |

*Primary Examiner*—A. Lionel Clingman
*Attorney, Agent, or Firm*—Edward McC. Roberts

[57] ABSTRACT

Dyes difficultly soluble or insoluble in water are used together with specific auxiliaries to dye or print textile material made from cellulose fibres, or mixtures thereof with synthetic fibres. These auxiliaries effect an increased dye yield, particularly on the cellulose material, and level tone-in-tone dyeings on mixed fabrics.

23 Claims, No Drawings

PROCESS FOR PRINTING OR PAD DYEING OF TEXTILE MATERIAL MADE FROM CELLULOSE FIBRES, OR FROM MIXTURES THEREOF WITH SYNTHETIC FIBRES

The present invention relates to a process for the printing or pad dyeing of textile material made from cellulose fibres, or from mixtures thereof with synthetic fibres, to the printing pastes or padding liquors for performing this process, and to the textile material printed or dyed by the process.

If mixed fibres made from cellulose and synthetic material are dyed with disperse dyes, the natural material does not become dyed but at most stained, whilst when dyeing with dyes well suited for dyeing the natural material, for example reactive or direct dyes, there results an inadequate dyeing of the synthetic material.

For the colour printing of mixed fibres of the above-mentioned type, there is therefore customarily used a printing paste which contains a dye mixture of the dyes suitable for the respective constituents of the mixed fibres; it is however seldom possible by this method to dye all the constituents of the mixed fibres in exactly the same shade.

From the Canadian Pat. No. 832,343 is known a process for printing mixed fibres made from cellulose and synthetic material, in which process both constituents of the mixed fibres are dyed with the same disperse dye, a printing paste being used which contains disperse dye, water and a polyalkylene glycol as solvent for the dye. The use of these solvents for the dye does not however in the case of many dyes, particularly in the case of the so-called organic pigment dyes, lead to satisfactory results, since the dissolving power of the polyalkylene glycols used is inadequate. This process is therefore practicable only with special disperse dyes. Furthermore, the solvents mentioned, especially the low-molecular solvents, are hygroscopic, so that the dried textile materials impregnated with the printing paste or padding liquor can easily become moist, and consequently tend to become smeared or stained before fixation.

The aim of the present invention was to develop a process for printing and pad dyeing textile material made from cellulose fibres, or mixtures thereof with synthetic fibres, by use of dyes difficultly soluble or insoluble in water, which process does not have the disadvantages mentioned above. This aim is achieved according to the invention by the concomitant use of selected auxiliaries.

The present invention thus relates to a process for printing or pad-dyeing textile material made from cellulose fibres, or mixtures thereof with synthetic fibres, using aqueous printing pastes or padding liquors, by impregnating the fibres, either simultaneously or successively, with (i) an aqueous dispersion of at least one dye difficultly soluble or insoluble in water, the dispersion optionally containing additives, and (ii) an aqueous solution of an auxiliary, and subsequently subjecting the printing or dyeing to a heat treatment, in which process there is used as an auxiliary (a) a compound of the formula I

wherein R is a group of the formula $-CO-(CH_2)_2-$ or $(CH_2)_n$, n being an integer from 3 to 6, and X is an $-NH$, $-O-$ or $-N-(CH_2)_m-OH$ group, m being an integer from nought to 4; or (b) a mixture or a complex of a lactam of the formula II

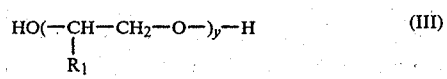

wherein n is an integer from 3 to 6, and a polyalkylene glycol of the formula III $$HO(-\underset{R_1}{CH}-CH_2-O-)_y-H \qquad (III)$$

wherein $R_1$ is hydrogen, a methyl or ethyl group, and y is an integer from 3 to 25.

Suitable compounds of the formula I

in which R is a $-CO-(CH_2)_2-$ group are for example succinic anhydride, succinimide, N-hydroxysuccinimide or N-(ω-hydroxyalkyl)-succinimide, where the alkyl group can have 1 to 4 carbon atoms.

When R in the above formula I is a $(CH_2)_n$ group, n being an integer from 3 to 6, the above compounds are lactams, lactones or N-substituted lactams, for example butyrolactam, valerolactam, caprolactam or enantholactam, butyrolactone, valerolactone, N-(β-hydroxyethyl)-caprolactam or N-(δ-hydroxypropyl)-caprolactam.

On account of being readily obtainable, preferred compounds amongst those mentioned are, inter alia, N-hydroxysuccinimide or succinimide, as well as the stated lactams, particularly δ-caprolactam.

Auxiliaries which can be used according to the invention are, besides the compounds of the formula I mentioned, preferably mixtures or complexes, and by virtue of their especially high dissolving capacity for the dye in particular the 1:1 molar complexes formed from a lactam of the formula II

wherein n is an integer from 3 to 6, and a polyalkylene glycol of the formula III

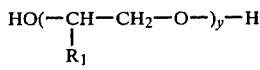

(III)

wherein $R_1$ is hydrogen or a methyl or ethyl group, and y is an integer from 3 to 25.

Suitable lactams of the formula II are butyrolactam, valerolactam, enantholactam and especially ε-caprolactam.

The polyalkylene glycols of the formula III are polybutylene glycols, preferably polyethylene glycols and polypropylene glcols. Particularly suitable among these are those of the formula IV

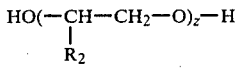

(IV)

wherein $R_2$ is hydrogen or methyl, and z is an integer from 5 to 10.

Preferred amongst the 1:1 molar complexes are those formed from ε-caprolactam and a polyethylene glycol or polypropylene glycol of the above-given formula IV.

When mixtures of a lactam of the above formula II and a polyalkylene of the above formula III are used, they are preferably mixtures of the components in the ratio of 80:20 to 20:80 percent by weight.

The auxiliaries usable according to the invention act as dye solvents, and they are produced by methods known per se. The 1:1 molar complexes of lactams and polyethylene glycols are obtained for example by dissolving the components in a suitable organic solvent or in water, if necessary with heating, and subsequently distilling off the organic solvent or water; or by mixing both components together by stirring until a clear solution is formed, heating being applied in the case where one or both compounds is (are) solid at room temperature.

It is advantageous to add to the auxiliary, particularly to the mixtures or complexes of lactam and polyalkylene glycol, 0.1 to 5 percent by weight, especially 0.5 to 1 percent by weight, relative to the weight of the auxiliary, of antioxidants. Antioxidants which can be used are for example: phenols, aromatic amines and hydroquinones, each of which is substituted by sterically hindering groups, such as di-tert-butyl-hydroxytoluene, tert-butylhydroxyanisole, 2,5-di-tert-butylhydroquinone, 3,5-di-tert-butylpyrocatechol; also alkylidene-bisphenols, such as 4,4'-methylene-bis-(2,6-di-tert-butyl-phenol), as well as hydroxylated thiodiphenyl ethers, O-, N- and S-benzyl compounds, hydroxybenzylated malonic esters, hydroxybenzyl aromatic hydrocarbons, s-triazine compounds, amides of β-(3,5-di-tert-butyl-4-hydroxyphenyl)-propionic acid, esters of β-(3,5-di-tert-butyl-4-hydroxyphenyl)-propionic acid, esters of β-(5-tert-butyl-4-hydroxy-3-methylphenyl)-propionic acid, esters of 3,5-di-tert-butyl-4-hydroxyphenylacetic acid, acylaminophenols, benzylphosphonates or preferably gallic acid propyl esters.

The addition of antioxidants reduces the oxidative thermal decomposition, especially of the polyalkylene glycol component.

This thermal decomposition is particularly high at temperatures over 200° C., and causes, besides an impairment of dye yield (on account of a reduced concentration of dye solvent in the fabric), an increased contamination of exhaust-air and possibly of apparatus.

Particularly preferred auxiliaries are the 1:1 molar complexes formed from ε-caprolactam and polypropylene glycol having a molecular weight of between 300 and 500, preferably about 400, which complexes contain 0.5 to 1 percent by weight, relative to the weight of the 1:1 molar complex, of gallic acid propyl ester.

The auxiliaries usable according to the invention are used preferably in an amount of 5–30 percent by weight, in particular 10–20 percent by weight, relative to the weight of the printing paste or padding liquor. They are added to the printing paste or padding liquor preferably before this is applied to the textile material to be dyed or printed. It is however also possible to apply the auxiliaries separately to the textile material, for example by printing, padding, slop-padding, immersion or spraying of the textile material with an aqueous solution of the auxiliary, either before or after impregnation of the textile material with the printing paste or padding liquor.

Suitable dyes for the process according to the invention have to be insoluble or difficultly soluble in water. They are for example the dyes described in the Colour Index as disperse dyes, vat dyes, solvent dyes, azoic dyes, or pigments. These can belong to various classes and are for example: nitro dyes, aminoketone dyes, ketone-imine dyes, methine dyes, nitrodiphenylamine dyes, quinoline dyes, aminonaphthoquinone dyes, coumarin dyes and in particular anthraquinone dyes and azo dyes, such as monoazo and disazo dyes. Suitable vat dyes are especially annularly-linked and heterocyclic benzo- and naphthoquinones, sulfur dyes and above all anthraquinoid and indigoid dyes.

Also optical brighteners are to be understood as being embraced by the term 'dyes'. They are for example: water-insoluble to difficultly water-soluble brighteners of the following classes of compounds: stilbenes, coumarins, benzocoumarins, pyrenes, pyrazines, oxazines, mono- or dibenzoxazolyl or -imidazolyl compounds, aryltriazole and v-triazole derivatives, as well as naphthalic acid imides.

The printing paste or padding liquor for carrying out the process according to the invention contains as a rule 45–95 percent by weight of water, 0.1 to 10 percent by weight of dye, 5–30 percent by weight of the defined compound (a) or (b), and 0.1 to 15 percent by weight, relative to the total weight, of further additives. It preferably contains 60–80 percent by weight of water, 1 to 8 percent by weight of the dye, 10–25 percent by weight of the compound (a) or (b) and 0.2 to 8 percent by weight of further additives.

Further additives are the antioxidants already mentioned, and also wetting agents, antifoaming agents or the agents influencing the properties of the textile material, for example softening agents, additives for imparting a flameproof finish, or agents rendering the textile material dirt-, water and oil-repellent, particularly however natural or synthetic thickeners. Suitable natural thickeners are for example carob bean flour ethers, starch ethers, alginates, starch, tragacanth, carboxymethylcellulose and cellulose ether. Suitable synthetic thickeners are for example high-molecular mono- or copolymers of acrylic acid, methacrylic acid, maleic acid with ethylenically unsaturated comonomers, such as ethylene, butadiene, hydroxyalkylacrylates, divinyldioxane and divinylbenzene, in the form of water-soluble alkali, ammonium or amine salts.

The content of thickener in the padding liquor is about 0.1–5 percent by weight; the printing pastes contain about 0.2 to 10 percent by weight of thickener, depending on the desired viscosity.

Textile material made from cellulose fibres or mixtures thereof with synthetic fibres can be dyed or printed by the process according to the invention, suitable cellulose fibres being those made from natural and regenerated cellulose, for example hemp, linen, jute, viscose silk, rayon fibres or in particular cotton. Suitable synthetic organic materials are for example: fibre materials made from synthetic polyamide, such as condensation products from hexamethylenediamine and adipic acid (polyamide 6.6) or sebacic acid (polyamide 6.10), also mixed condensation products, for example from hexamethylenediamine, adipic acid and ε-caprolactam (polyamide 6.6/6), in addition polymerisation products from ε-caprolactam or from ω-aminoundecanoic acid. Also applicable is polyester material, for example linear high-molecular esters of aromatic polycarboxylic acids with polyfunctional alcohols, for example those from terephthalic acid and ethylene glycol or dimethylolcyclohexane, as well as mixed polymers from terephthalic acid and isophthalic acid and ethylene glycol. And finally also cellulose $(2\frac{1}{2})$-acetate and cellulose triacetate fibres are suitable synthetic fibre materials.

There is preferably dyed or printed by the process according to the invention textile material made from fibre mixtures consisting of 2 constituents, especially fibre mixtures of polyester and cotton; it is however also possible to use fibre mixtures containing, in addition to cellulose, two or more of the fibre materials mentioned above. The textile material can for example be in the form of fabrics, looped fabric, such as knitted goods or knitwear, or fleece.

The textile material is printed or padded in the known manner with the printing paste or padding liquor and subsequently dried. The dyes on the mixed fabric are afterwards fixed, for example by heating for 30 to 120 seconds at 190° to 225° C., preferably for 60 seconds at 210°-215° C., or by steaming, for example under normal pressure with superheated steam at 170° to 200° C. for 3 to 12, preferably 5 to 8, minutes, or with steam at 1.5 bars excess pressure for 15 to 30 minutes.

The material after fixing is finished in the customary manner. There are obtained by this process level printings or dyeings with a good dye yield. Very level tone-in-tone dyeings are obtained on mixtures of cellulose fibres and synthetic fibres.

Compared with polyalkylene glycols, the complexes of lactams with polyalkylene glycols used in the present process have an increased dissolving power for water-insoluble dyes, particularly for pigment dyes, a property which leads to a better dye yield after fixation of the dyes, especially on cellulose material. But also on synthetic material the dye yield is higher than when dyeing is performed without auxiliary or just with polyalkylene glycols. Furthermore, the complexes are less hygroscopic than the individual components, so that the printings or dyeings become less readily moist before fixation, and do not therefore tend to become smeared or stained. Finally, the complexes are better biologically degradable, since the lactam component is more readily degradable than the polyalkylene glycol component.

The following Examples serve to further illustrate the process according to the invention. Parts are parts by weight and the temperatures are given in degrees Centigrade.

EXAMPLE 1

A mixed fabric consisting of 50% of cotton and 50% of polyester and having a weight per square meter of 120 g is printed, in the roller printing process, with a printing paste comprising
15 parts of the dye, Pigment Yellow 1 (CI 11680), as a 20% liquid commercial product,
500 parts of an 8% Na-alginate thickening,
150 parts of caprolactam,
2 parts of citric acid, and
333 parts of water.

The material is subsequently dried at 110°, and the printing is fixed for 60 seconds at 215° in hot air. The fabric is afterwards rinsed with water, treated with a hot soap solution and again rinsed with water. The result is a level printing having good fastness properties.

When the printing is carried out without caprolactam, the resulting printing is clearly paler and unsettled.

EXAMPLE 2

An equally good printing is obtained by proceeding as in Example 1 but using, instead of caprolactam, the same amount of the 1:1 molar complex of caprolactam with polyethylene glycol (molecular weight 400), which has been obtained by the mixing together of the two components.

EXAMPLE 3

A mixture fabric made from 67 parts of polyester and 33 parts of cotton is printed, in the screen printing process, with a printing paste consisting of
30 parts of the dye (as a 33% liquid commercial preparation) of the formula

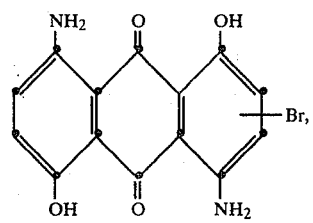

500 parts of an alginate thickening (3%),
1 part of citric acid,
200 parts of caprolactam, and
269 parts of water,
and the printing is treated after drying for 6 minutes at 190° in superheated steam. The printing obtained after subsequent rinsing with cold water and with hot soap solution has a level deep blue colour, the cotton and polyester fibres being dyed in the same shade.

EXAMPLE 4

A cotton/polyester mixed fabric made up of 50 parts of cotton and 50 parts of polyester is impregnated in a padding machine and pressed out to 90% liquor absorption, the liquor used consisting of
100 parts of a 1:1 molar complex of caprolactam and polyethylene glycol (molecular weight 300), and
900 parts of water.

The material is subsequently dried at 100° and is then printed with a printing paste consisting of
80 parts of the dye, Pigment Red 112 (CI 12370), as a 20% liquid commerical preparation,
500 parts of an Na-alginate thickening (12%), and 420 parts of water.

The printing after drying is fixed for 60 seconds at 215°. The unfixed dye can be removed by cold and hot rinsing.

The resulting red printing has good fastness properties and a good tone-in-tone dyeing on the two fibre constituents.

EXAMPLE 5

When the procedure is carried out as described in Example 4 except that there are used, instead of 100 parts of the 1:1 molar complex of caprolactam and polyethylene glycol (molecular weight 300), 100 parts of the same complex containing however additionally 1% of gallic acid propyl ester as antioxidant, the results are a somewhat deeper dyeing and a reduced generation of smoke from the fixed fabric compared with the results obtained on use of the complex without antioxidant. The stabilising effect of the antioxidant is shown also when the above-mentioned molar complex, as well as the same complex containing 1% of gallic acid propyl ester, is heated at a heating rate of 20°/min. to 225°. The weight loss in the case of the unstabilised complex is 42.5%, whereas in the case of the stabilised complex it is only 30.9%.

EXAMPLE 6

A mixed fabric comprising 67 parts of polyester and 33 parts of cotton is slop-padded with an aqueous liquor consisting of
60 parts of Pigment Red 7 (CI 12420), in the form of a 20% liquid commercial preparation,
1 part of highly viscous sodium alginate,
1 part of 80% acetic acid,
150 parts of a 1:1 molar complex of caprolactam and polypropylene glycol (molecular weight 400), stabilised with 1% of thiodiethylene glycol-$\beta$-[3,5-di-t.-butyl-4-hydroxyphenyl]-propionate as an antioxidant, and
788 parts of water,
and the fabric is squeezed out to a liquor absorption of 65% of the weight of the fibres. The fabric is then dried for 2 minutes at 120°, and is subjected to the thermosol process for 1 minute at 210°. The fabric is subsequently soaped for 10 minutes at 98° with a liquor containing per liter 1 g of an anionic alkyl ether sulfate and 1 g of calcined sodium carbonate, and finally rinsed. The result is an even brilliant red dyeing on both fibre constituents with good fastness properties.

EXAMPLE 7

A mixed fabric comprising 50 parts of polyester and 50 parts of cotton is slop-padded with an aqueous liquor consisting of
60 parts of Pigment Yellow (CI 11680) in the form of a 20% liquid commercial preparation,
1 part of highly viscous sodium alginate,
1 part of 80% acetic acid,
150 parts of valerolactam, and
788 parts of water,
and the material is squeezed out to a liquor absorption of 70% of the weight of the fibres. The fabric is then dried for 2 minutes at 120° and subsequently subjected to the thermosol process for 1 minute at 210°. The fabric is afterwards soaped at 98° for 10 minutes with a liquor containing per liter 1 g of an anionic alkyl ether sulfate and 1 g of calcined sodium carbonate, and finally rinsed.

The result is a level brilliant red dyeing on both fibre constituents with good fastness properties.

A fabric consisting of 100% of cotton and a fabric consisting of 100% of polyester are dyed in a similar manner. The cotton fabric is washed in exactly the same manner as the mixed fabric polyester/cotton, and the 100% polyester fabric is washed for 15 minutes at 70° with a liquor containing per liter 5 ml of NaOH (36° Be), 3 g of hydrosulfite and 1 g of an alkylaminopolyglycol ether.

A brilliant yellow dyeing having good fastness properties is obtained on both fibre materials.

EXAMPLE 8

If the procedure is carried out as described in Example 7 except that there are used, instead of 150 g of valerolactam, identical amounts of enantholactam, of succinimide or of the 1:1 molar complex of valerolactam with polyethylene glycol (molecular weight 300), there are obtained equally good dyeings.

EXAMPLE 9

When the procedure is carried out as described in Example 7 except that the dye used is "Küpengelb 2" (CI 67300) or the yellow dye of the formula

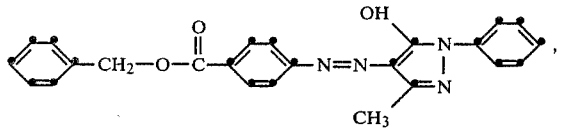

equally good tone-in-tone dyeings are obtained.

EXAMPLES 10–16

A polyester/cotton mixed fabric (67:33) is impregnated on a padding machine and pressed out to 70% liquor absorption, the liquor used consisting of
6 parts of one of the dyes listed in the following Table,
10 parts of Na-alginate thickening 1:100,
2 parts of a wetting agent (aqueous mixture containing coconut fatty acid diethanolamide and ethoxylated nonylphenol),
0.1 part of 80% acetic acid,
15 parts of a 1:1 molar complex of caprolactam and polypropylene glycol (molecular weight about 400), and
66.9 parts of water.

The material is subsequently dried at 120° for 2 minutes, and subjected to the thermosol process for 1 minute at 210°. The material is afterwards washed for 10 minutes at boiling temperature with a liquor containing per liter 1 g of nonylphenol diglycol ether sulfate and 1 g of sodium carbonate.

Level dyeings on both fibre constituents in the given shades and with good fastness properties are obtained.

| Ex. | Dye | Shade on PES/CO |
|---|---|---|
| 10 | Pigment Red 4; CI 12085 | red |
| 11 | $O_2N-\underset{}{\bigcirc}-N=N-CH(COCH_3)-CO-NH-\underset{OCH_3}{\underset{}{\bigcirc}}$ (with OCH$_3$ substituents) | yellow |

-continued

| Ex. | Dye | Shade on PES/CO |
|---|---|---|
| 12 | Pigment Red 7; CI 12420 | red |
| 13 | 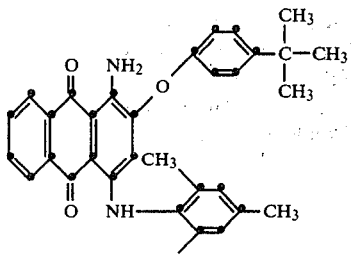 | violet |
| 14 | 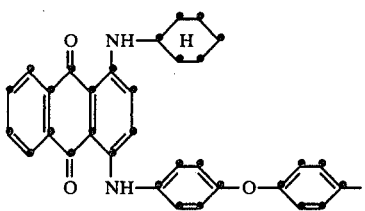 | blue |
| 15 | 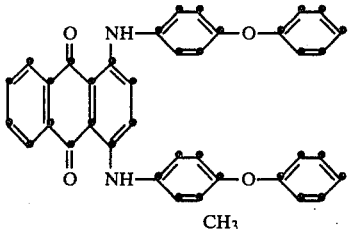 | green |
| 16 | 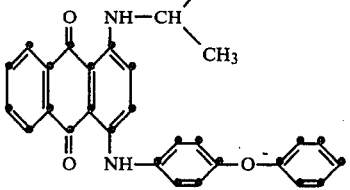 | blue |

When the procedure is carried out as described in Examples 10–16 except that a padding liquor without the 1:1 molar complex of caprolactam and polypropylene glycol is used, very unlevel dyeings are obtained, since the cotton constituent is virtually undyed.

What is claimed is:

1. A process for printing or pad-dyeing textile material made from cellulose fibers, or mixtures thereof with synthetic fibers, comprising the steps of impregnating the fibers, either simultaneously or successively, with (i) an aqueous dispersion of at least one dye which is difficultly soluble or insoluble in water and (ii) an aqueous solution of an auxiliary, and subsequently subjecting the impregnated fibers to a dye-fixing heat treatment, wherein the auxiliary is a mixture or a complex of a lactam of the formula

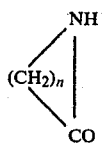

wherein n is an integer from 3 to 6, and a polyalkylene glycol of the formula

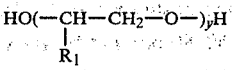

wherein $R_1$ is hydrogen, methyl or ethyl, and y is an integer from 3 to 25.

2. The process of claim 1, wherein the auxiliary is the 1:1 lactam-polyalkylene glycol molar complex.

3. The process of claims 1 or 2, wherein $R_1$ is hydrogen or methyl and y is an integer from 5 to 10.

4. The process of claim 3, wherein n is 5.

5. The process of claim 1 wherein the auxiliary is the lactam-polyalkylene glycol mixture.

6. The process of claim 1, wherein the mixture has a lactam:polyalkylene glycol weight ratio of 20:80 to 80:20.

7. The process of claim 1, wherein one of (i) or (ii) additionally contains 0.1 to 5 percent by weight of an antioxidant, relative to the weight of the auxiliary.

8. The process of claim 7, wherein the antioxidant is propyl gallate.

9. The process of claim 1, wherein the fibers are impregnated with a printing paste or padding liquor which contains 5 to 30% by weight of the auxiliary.

10. The process of claim 2, wherein n is 5, the polyalkylene glycol is polypropylene glycol having a molecular weight of between 300 and 500, and one of (i) or (ii) contains 0.5 to 1 percent by weight of propyl gallate relative to the weight of an auxiliary.

11. The process of claim 1, wherein the textile material is made from cellulose fibers in admixture with polyester fibers.

12. The process of claim 1, wherein the impregnated fibers are dried at 80° C. to 130° C., and subsequently heated at 150° to 225° C.

13. A printing paste or padding liquor which contains water, a dye difficultly soluble or insoluble in water, and an auxiliary which is a mixture or a complex of a lactam of the formula

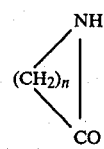

wherein n is an integer from 3 to 6, and a polyalkylene glycol of the formula

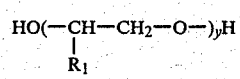

wherein $R_1$ is hydrogen, methyl or ethyl, and y is an integer from 3 to 25.

14. The printing paste or padding liquor of claim 13 wherein the auxiliary is the 1:1 lactam-polyalkylene glycol molar complex.

15. The printing paste or padding liquor of claim 14 wherein n is 5, $R_1$ is hydrogen or ethyl, and y is an integer from 5 to 10.

16. The printing paste or padding liquor of claim 13, which contains 45 to 95 percent by weight of water, 0.1 to 10 percent by weight of dye, 5 to 30 percent by weight of the auxiliary, and 0.1 to 15 percent by weight of a further additive.

17. The printing paste or padding liquor of claim 16, which contains 60–80 percent by weight of water, 1 to 8 percent by weight of dye, 10 to 25 percent by weight of the auxiliary and 0.2 to 8 percent by weight of the further additive.

18. The printing paste or padding liquor of claims 16, which contains a thickener, an antioxidant, or both, as the further additive.

19. The printing paste or padding liquor of claim 18, which contains 0.1 to 10 percent by weight of thickener.

20. The printing paste or padding liquor of claim 18, which contains 0.1 to 5 percent by weight of antioxidant, relative to the weight of the auxiliary.

21. The textile material printed or dyed by the process of claim 1.

22. The process of claim 1, wherein one of (i) or (ii) additionally contains 0.5 to 1 percent by weight of an antioxadant, relative to the weight of the auxiliary.

23. The process of claim 10, wherein the polypropylene glycol has a molecular weight of about 400.

* * * * *